United States Patent [19]

Miyasaka et al.

[11] Patent Number: 4,473,692
[45] Date of Patent: Sep. 25, 1984

[54] CAMPTOTHECIN DERIVATIVES AND PROCESS FOR PREPARING SAME

[75] Inventors: Tadashi Miyasaka, Kanagawa; Seigo Sawada, Tokyo; Kenichiro Nokata, Tokyo; Masahiko Mutai, Tokyo, all of Japan

[73] Assignee: Kabushiki Kaisha Yakult Honsha, Tokyo, Japan

[21] Appl. No.: 413,879

[22] Filed: Sep. 1, 1982

[30] Foreign Application Priority Data

Sep. 4, 1981 [JP] Japan .................................. 56-138410
Sep. 4, 1981 [JP] Japan .................................. 56-138411
Feb. 5, 1982 [JP] Japan .................................... 57-16370
Mar. 5, 1982 [JP] Japan .................................... 57-34094

[51] Int. Cl.³ .................. C07D 491/147; A61K 31/47
[52] U.S. Cl. ..................................... 546/48; 424/258; 204/158 R
[58] Field of Search ......................................... 546/48

[56] References Cited

U.S. PATENT DOCUMENTS 4,399,276 8/1983 Miyasaka et al. ................... 542/416
4,399,282 8/1983 Miyasaka et al. ...................... 546/48

FOREIGN PATENT DOCUMENTS 56692 7/1982 European Pat. Off. .
3027172 2/1981 Fed. Rep. of Germany .
116015 7/1982 Japan .

OTHER PUBLICATIONS

Pan, et al., Chemical Abstracts, vol. 84, 115629p (1976).
Shanghai Institute, Chemical Abstracts, vol. 92, 209148y (1980).
Wani, et al., J. Med. Chem., vol. 23, No. 5, pp. 554–560 (1980).
Kametani, et al., Chemical Abstracts, vol. 95, 115821x (1981).
Miyasaka, et al., Heterocycles, vol. 16, No. 10, pp. 1713–1717 (1981).

Primary Examiner—Donald G. Daus
Assistant Examiner—Diana G. Rivers
Attorney, Agent, or Firm—Birch, Stewart, Kolasch & Birch

[57] ABSTRACT

New Camptothecin derivatives possessing high antitumor activity with slight toxicity, represented by the general formula:

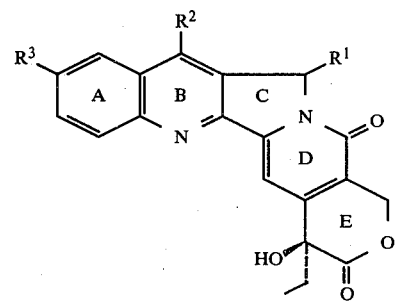

wherein $R^1$ is a hydrogen atom, an alkyl group, a hydroxyl group, an alkoxy group or an acyloxy group, $R^2$ for a hydrogen atom, an alkyl group, an aralkyl group, a hydroxymethyl group, a carboxymethyl group or an acyloxymethyl group, and $R^3$ is the grouping —XR′ (where R′ is a hydrogen atom, an alkyl group or an acyl group and X is an oxygen atom or a sulfur atom), a nitro group, an amino group, an alkylamino group, an acylamino group or a halogen atom, with the proviso that when both of $R^1$ and $R^2$ are hydrogen atoms, $R^3$ should not be a hydroxyl group, methoxy group or acetoxy group. These new camptothecin derivatives are prepared by treating a 5-$R^1$-7-$R^2$-camptothecin derivative with a peroxidant and then reacting the resultant 5-$R^1$-7-$R^2$-camptothecin-1-oxide with an active hydrogen compound under irradiation of UV-rays or by catalytically hydrogenating the ring B of camptothecin in a solvent, treating the resultant tetrahydro product with an acylating agent, introducing a nitro group into the 10-position of the acylated product by the reaction with nitric acid, splitting off the acyl group in the 10-nitro product by hydrolysis and treating the hydrolyzed tetrahydro product with an oxidizing agent for dehydrogenation, and if desired, reducing the nitro group in the resulting product to an amino group and modifying the amino group by N-alkylation, N-acylation or by diazotization followed by hydrolysis or the Sandmeyer reaction, before or after the oxidation of the 10-nitro-tetrahydro product.

41 Claims, No Drawings

CAMPTOTHECIN DERIVATIVES AND PROCESS FOR PREPARING SAME

BACKGROUND OF THE INVENTION

1. Field of the Invention

This invention relates to new 10-substituted camptothecin derivatives possessing anti-tumor activity (including carcinostatic activity) and to processes for the preparation of such derivatives. More particularly, this invention relates to new 5-$R^1$-7-$R^2$-camptothecin derivatives carrying a substituent $R^3$ in the 10-position thereof and possessing anti-tumor activity with a low level of toxicity as well as processes for the preparation of 10-substituted camptothecin derivatives.

2. Description of the Prior Art

Camptothecin is a cytotoxic alkaloid isolated from leaves and barks of *Camptotheca accuminata* (Nyssaceae), a plant native to China, which has a pentacyclic structure consisting of a characteristic fused 5-ring system of quinoline (rings A and B), pyrroline (ring C), α-pyridone (ring D) and a six-membered lactone (ring E) and is distinguished by displaying a strong inhibitory activity toward biosynthesis of nucleic acid. In addition, camptothecin is a unique anti-tumor substance characterized by its rapid and reversible action and its lack of any cross-tolerance with the existing anti-tumor agents and by exhibiting a strong anti-tumor activity against experimentally transplanted carcinoma such as leukemia L-1210 in mice or Walker 256 tumor in rats. Although camptothecin is still regarded as one of the most potent substances possessing anti-tumor activity, the use of this compound itself for clinical treatments is significantly limited because of high toxicity.

Accordingly, a number of attempts have been made to reduce the toxicity of camptothecin while maintaining its anti-tumor activity by converting camptothecin chemically into its derivatives. The chemical modifications so far reported mainly concern the rings D and/or E of camptothecin, but the results of such modifications revealed only failure in maintaining expected anti-tumor activity and poor improvement in toxicity [J. Med. Chem., 19 (1976), 675]. From the chemotherapeutic point of view, therefore, it is of importance that the chemical modifications of camptothecin should be restricted in the rings A, B and C without effecting any change in the rings D and E which are conceivable to be one of the essential structural elements for the expression of the above mentioned characteristic biological activities.

Except for a method for functionalizing the 12-position of camptothecin reported in 1976 which comprises a series of troublesome conversion and purification operations starting with nitration at the 12-position [P. Pei-chuang et al., Hau Hsueh Hsueh Pao 33 (1975) 71; Chem. Abstr. 84 (1976) 115629p], however, no success was reported until 1979 in connection with chemical functionalization of camptothecin in a moiety involving the rings A, B and C. This is probably ascribable to the reasons that camptothecin itself is only sparingly soluble in various organic solvents and that camptothecin possessing the nature of heterocyclic rings in its molecule is resistant to the so-called electrophilic reactions conventionally carried out on aromatic rings. In the present status, such obstacles strongly discourage chemical modifications of camptothecin contemplated intellectually of preparing new classes for derivatives thereof.

Under the above mentioned circumstances, the present inventors previously found together with co-workers processes for preparing 5- and 7-substituted camptothecins (U.S. Pat. No. 4,399,282) by introducing (1) hydroxymethyl group into 7-position of camptothecin by subjecting camptothecin to a radical reaction with methanol by the aid of sulfuric acid and a peroxide (such as potassium persulfate, sodium persulfate, ammonium persulfate, hydrogen peroxide or a tertiary-butyl peroxide) wherein the reaction is carried out usually by dissolving camptothecin in an aqueous solution of methanol-sulfuric acid, adding thereto a peroxide as a radical reaction initiator (Japanese Laid-open Patent Appln. No. 56-12391), (2) hydroxy group into 5-position of camptothecin by treating camptothecin with sulfuric acid, water and a persulfate (such as sodium persulfate, potassium persulfate and ammonium persulfate) in the presence of a metal ion (such as silver salts such as silver nitrate, silver sulfate, silver carbonate or silver acetate or a ferrous salt such as ferrous sulfate, ferrous chloride and ferrous oxide) under heat and agitation (Japanese Laid-open Patent Appln. No. 56-12392), and (3) an alkyl or aralkyl group into 7-position of camptothecin efficiently in a single step by subjecting camptothecin to a radical reaction with a compound of the general formula: RX (wherein R stands for an alkyl group or an aralkyl group, and X for —CH$_2$OH, —COOH, —CHO, —CO—R or

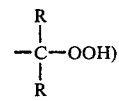

preferably in a large excess amount by the aid of sulfuric acid, water and a peroxide (such as hydrogen peroxide or tert-butylhydroperoxide) in the presence of a metal ion (such as ferrous sulfate, ferrous chloride or ferrous oxide) usually under ice-cooling and agitation and thereafter stirring while warming the mixture to room temperature (Japanese Laid-open Patent Appln. No. 56-158786). Further, the present inventors prepared together with co-workers a great number of new camptothecin derivatives possessing anti-tumor activity with slight toxicity from these 5- and 7-substituted camptothecin derivatives (U.S. Pat. Nos. 4,399,276 and 4,399,282) according to the process wherein 7-hydroxymethylcamptothecin is acylated with an acylating agent usually capable of acylating hydroxy group, for example, a halide of a carboxylic acid (such as formic acid, acetic acid, propionic acid, butyric acid, phenylacetic acid, succinic acid, trifluoroacetic acid or the like aliphatic carboxylic acid or benzoic acid or the like aromatic carboxylic acid) or a carboxylic acid anhydride whereby the hydroxy group or groups of the camptothecin is acylated to obtain 7-acyloxymethylcamptothecins or 20-O-acyl-7-acyloxymethylcamptothecins or wherein 7-hydroxymethylcamptothecin is oxidized with an oxidizing agent usually capable of oxidizing hydroxymethyl group to carboxy group, for example, an anhydrous chromate, a bichromate or a permanganate whereby 7-carboxycamptothecin is obtained, which is then esterified according to a usual manner with an alcohol (such as methanol, ethanol, propanol or butanol) to obtain 7-alkoxycarbonylcamptothecins (Japanese Laid-open Patent Appln. No. 56-12393), the process wherein 5-alkoxycamptothecins are obtained by dissolving 5-hydroxycamptothecin in a lower alcohol (such as methanol, ethanol, propanol or butanol), adding thereto an acid (such as hydrochloric acid, sulfuric acid or boron fluoride etherate) as catalyst, and heating the mixture, or wherein 5-acyloxycamptothecins or 20-O-acyl-5-acyloxycamptothecins are obtained by acylating 5-hydroxycamptothecin with a reactive acid derivative such as a halide of a carboxylic acid (such as formic acid, acetic acid, propionic acid, butyric acid, phenylacetic acid, succinic acid or trifluoroacetic acid or benzoic acid) or an acid anhydride (Japanese Laid-open Patent Appln. No. 56-12394), the process wherein camptothecin-7-aldehyde is obtained directly from the 7-hydroxymethylcamptothecin by treating the 7-hydroxymethylcamptothecin with various cationoid reagents without using any oxidizing agent [The cationoid reagent includes a variety of mineral acids (such as sulfuric acid, hydrochloric acid, perchloric acid, hydrobromic acid and the like), organic acids (such as acetic acid, propionic acid, benzoic acid, monochloroacetic acid, trifluoroacetic acid, p-toluenesulfonic acid and methanesulfonic acid), Lewis acids (such as boron trifluoride-ether, aluminum chloride and stannic chloride), organic acid halides (such as p-toluenesulfonyl chloride, phenylacetyl chloride and the like) and chlorinating agents (such as phosphorus oxychloride, thionyl chloride and the like inorganic acid chlorides) and is preferably used in a solvent such as water, dimethylformamide or dioxane at a temperature of 90°–100° C. or under reflux] (Japanese Laid-open Patent Appln. No. 57-116075), and the process wherein 7-alkoxymethylcamptothecins and 7-dialkoxymethylcamptothecins are obtained by treating 7-hydroxymethylcamptothecin in a lower alcohol (such as methanol, ethanol, n-propanol, isopropanol, n-butanol, isobutanol, t-butanol, n-amyl alcohol, isoamyl alcohol or t-amyl alcohol) or an aralkyl alcohol (such as benzyl alcohol, phenethyl alcohol or phenylpropanol) with an acid (such as sulfuric acid, hydrochloric acid, hydrobromic acid, perchloric acid; Lewis acids, for example, boron trifluoride aluminum chloride and stannic chloride; trifluoroacetic acid, trichloroacetic acid, benzenesulfonic acid, toluenesulfonic acid or methanesulfonic acid) at a temperature from room temperature to the boiling reflux temperature from room temperature to the boiling reflux temperature under such condition that the use of the acid in a catalytic amount or several molar equivalent amount affords a 7-dialkoxymethylcamptothecin exclusively or preferentially, but the use of the acid in a large excess amount, e.g. in a 150–250 molar equivalent amount affords a 7-alkoxymethylcamptothecin exclusively or preferentially (In the event that both of a 7-dialkoxymethylcamptothecin and a 7-alkoxymethylcamptothecin are formed concurrently, both products can be separated and purified by subjecting them to column chromatography on silica gel or high speed fluid chromatography) (Japanese Laid-open Patent Appln. No. 57-116076). However, the sorts of camptothecin derivatives prepared according to these processes are still limitative.

Noteworthy in recent years is that 10-hydroxycamptothecin isolated from Camptotheca acuminata was reported to be lower in toxicity than camptothecin itself but higher in anti-tumor activity (a certain medical magazine in China, 1978). For further extensive researches on the relation between substituents in camptothecin derivatives and anti-tumor activity and/or toxicity, therefore, there is still a great demand in this art for developing further new classes of camptothecin derivatives possessing a low level of toxicity while maintaining the inherent anti-tumor activity by chemical modifications of camptothecin itself or derivatives thereof in a simple manner.

BRIEF SUMMARY OF THE INVENTION

Accordingly, it is an object of the present invention to provide new 10-substituted camptothecin derivatives.

It is another object of the present invention to provide new 10-substituted camptothecin derivatives which are strong in anti-tumor activity and possess good absorbability in living bodies with very low toxicity.

It is still another object of the present invention to provide processes for the preparation of various 10-substituted camptothecin derivatives.

It is a further object of the present invention to provide new means for introducing a substituent into the 10-position of camptothecin or a derivative thereof.

Other objects, features and advantages of the present invention will become apparent more fully from the following description.

DETAILED DESCRIPTION OF THE INVENTION

With a view to preparing a new class of camptothecin derivatives possessing the inherent anti-tumor activity with extremely reduced toxicity, the present inventors have made further researches for chemically modifying the 10-position of camptothecin or 5- and/or 7-substituted derivatives thereof already prepared by the present inventors and co-workers, paying careful attention to these chemical modifications in order to avoid any destruction of the structure of the rings D and E. As a result of this further research, it has been found surprisingly that an alkoxy group, an acyloxy group or hydroxyl group can be introduced into the 10-position of camptothecin or a 5- and/or 7-substituted derivative thereof by treating camptothecin or a 5- and/or 7-substituted derivative thereof with a peroxidant and then reacting the resultant N-oxide compound with an active hydrogen compound in the presence of an acid under irradiation of UV-rays.

In addition, the present inventors have conducted research for developing a method for introducing a hydroxy group, a nitrogen-containing substituent (such as a nitro group or amino group) or a halogen atom into the 10-position of camptothecin. As a result of this work, it has also been found surprisingly that a nitro group can be introduced into the 10-position of camptothecin by catalytically hydrogenating camptothecin in a liquid vehicle such as acetic acid or dioxane-acetic acid in the presence of a noble metal catalyst, such as platinum oxide catalyst, treating the resultant 1, 2, 6, 7-tetrahydrocamptothecin with an acylating agent, and then treating the thus obtained 1-acyl-1, 2, 6, 7-tetrahydrocamptothecin with conc. nitric acid in the presence of sulfuric acid, and that the nitro group in the 10-position of the resultant 1-acyl-10-nitro-1, 2, 6, 7-tetrahydrocamptothecin can be converted preferably after removing the acyl group by hydrolysis and oxidation for dehydrogenation of the saturated ring, into the free amino group by reduction and the amino group can further be converted, according to a variety of methods, known per se, into an alkylamino group by alkylation, into an acylamino group by acylation or into hydroxyl or a halogen substituent by diazotization followed by hydrolysis or a Sandmeyer reaction.

The new class of 10-substituted camptothecins and 5- and/or 7-substituted derivatives thereof thus obtained are also provided with anti-tumor activity and extremely reduced toxicity. The present invention has been accomplished on the basis of the above finding.

In accordance with the present invention, there are provided new 10-substituted camptothecin derivatives of the general formula:

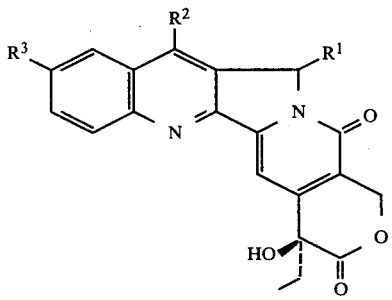

wherein $R^1$ is a hydrogen atom, an alkyl group, a hydroxyl group, an alkoxy group or an acyloxy group, $R^2$ is a hydrogen atom, an alkyl group, an aralkyl group, a hydroxymethyl group, a carboxymethyl group or an acyloxymethyl group, and $R^3$ is the grouping —XR' (where R' is a hydrogen atom, an alkyl group or an acyl group and X is an oxygen atom or a sulfur atom), a nitro group, an amino group, an alkylamino group, an acylamino group or a halogen atom, with the proviso that when both of $R^1$ and $R^2$ are hydrogen atoms, $R^3$ should not be a hydroxyl group, methoxy group or acetoxy group.

In the above general formula (I), either one of the substituents $R^1$ and $R^2$ is preferably a hydrogen atom. When $R^1$, $R^2$ or R' is an alkyl group, it generally has 1-30 carbon atoms. In view of the availability of alkylating reactants, the alkyl group has preferably 1-18 carbon atoms. Illustrative of the alkyl group are, for example, straight or branched chain alkyl groups with 1-30, preferably 1-18 carbon atoms, such as methyl, ethyl, n-propyl, isopropyl, n-butyl, isobutyl, sec-butyl, tert-butyl, n-pentyl, isopentyl, n-hexyl, n-heptyl, n-octyl, 2-ethylhexyl, n-nonyl, n-decyl, undecyl, dodecyl, myristyl, heptadecyl, octadecyl and eicosyl groups. When the alkyl groups are branched, the branched chains may be combined together to form a cycloalkyl group such as cyclopentyl, cyclohexyl, cycloheptyl or cyclooctyl group. When $R^1$ is an alkoxy group, the alkyl moiety thereof generally corresponds to the aforesaid alkyl group. Preferable examples of the alkoxy group are those derived from straight or branched chain lower alkyl groups with 1-8 carbon atoms, such as methoxy, ethoxy, n-propoxy, isopropoxy, n-butoxy, isobutoxy, sect-butoxy, tert-butoxy, n-pentyloxy, isopentyloxy, n-hexyloxy, n-heptyloxy, n-octyloxy and 2-ethylhexyloxy groups. When $R^1$ is an acyloxy group, the alkyl moiety thereof generally corresponds to the aforesaid straight or branched chain alkyl group with 1-17 carbon atoms, such as acetoxy, propionyloxy, n-butyryloxy, isobutyryloxy, valeryloxy, hexanoyloxy, heptanoyloxy, octanoyloxy, nonanoyloxy, decanoyloxy, undecanoyloxy, dodecanoyloxy, pentadecanoyloxy, hexadecanoyloxy, heptadecanoyloxy and octadecanoyloxy groups. The acyloxy group includes the formyloxy group as well. The acyl moiety of the acyloxy group may be derived from aromatic carboxylic acids, heterocyclic carboxylic acids, aralkylcarboxylic acids and alkyl and aromatic sulfonic acids. These acids may contain one or more unsaturated bonds in the molecule and carry one or more substituents such as halogen atoms, amino groups and hydroxyl groups. Illustrative of these acids other than the aliphatic carboxylic acids mentioned in the above acyloxy groups are, for example, benzoic acid, nucleus-substituted benzoic acids, nicotinic acid, phenylacetic acid, ethanesulfonic acid, nucleus-substituted or -unsubstituted benzenesulfonic acids, various kinds of amino acids and halogen-substituted aliphatic acids such as monochloroacetic acid. When $R^2$ is an aralkyl group, preferable examples thereof include benzyl, phenethyl, phenylpropyl and 1- or 2-naphthylmethyl groups as well as their nucleus-substituted homologues. When $R^2$ is an acyloxymethyl group, the acyl moiety generally corresponds to the aforementioned acyl group. Preferable examples of the acyloxymethyl group include those having the acyl moiety with 1-8 carbon atoms, such as acetoxymethyl, ethanesulfonyloxymethyl, propionyloxymethyl, butyryloxymethyl, hexanoyloxymethyl, heptanoyloxymethyl, p-toluenesulfonyloxymethyl, benzoyloxymethyl, phenylacetoxymethyl, nicotinoyloxymethyl and monochloroacetoxymethyl groups. When R' is an acyl group, it generally corresponds to the acyl group mentioned with respect to the case of $R^1$ being an acyloxy group. When R' is an alkylamino group, the alkyl moiety is preferably a lower alkyl group with 1-8 carbon atoms. Illustrative of the alkylamino group are, for example, methylamino, ethylamino, propylamino, isopropylamino, n-butylamino, tert-butylamino, pentylamino, hexylamino, heptylamino and octylamino groups. When R' is an acylamino group, the acyl moiety generally corresponds to the acyl group mentioned with respect to the case of $R^1$ being an acyloxy group. Preferable examples of halogen atoms include chlorine and bromine atoms.

The above mentioned alkyl and alkoxy groups may contain, as in the case of acyl or acyloxy groups, one or more substituents such as chloro, nitro, amino, carboalkoxy, alkylamino, dialkylamino and alkoxy groups.

The new 10-substituted camptothecin derivatives of the present invention represented by the general formula (1) possess anti-tumor activity with reduced toxicity. Illustrative of 10-substituted camptothecin derivatives obtained by this invention are 10-hydroxycamptothecin (10-hydroxy-CPT; "camptothecin" is referred to hereinafter simply as "CPT"), 10-methoxy-CPT, 10-ethoxy-CPT, 10-butoxy-CPT, 10-octyloxy-CPT, 10-acetoxy-CPT, 10-propionyloxy-CPT, 10-hexanoyloxy-CPT, 10-[(carboethoxymethyl)thio]CPT, 10-hydroxy-5-methyl-CPT, 10-hydroxy-5-ethyl-CPT, 10-hydroxy-5-methoxy-CPT, 10-hydroxy-5-propoxy-CPT, 10-hydroxy-5-acetoxy-CPT, 10-hydroxy-7-hydroxymethyl-CPT, 10-hydroxy-7-methyl-CPT, 10-hydroxy-7-ethyl-CPT, 10-hydroxy-7-propyl-CPT, 10-hydroxy-7-benzyl-CPT, 10-hydroxy-7-acetoxymethyl-CPT, 10-methoxy-5-ethyl-CPT, 10-methoxy-7-ethyl-CPT, 10-acetoxy-7-benzyl-CPT, 10-propionyloxy-7-octanoyloxy-CPT, 10-nitro-CPT, 10-nitro-5-ethyl-CPT, 10-nitro-7-benzyl-CPT, 10-nitro-7-acetoxymethyl-CPT, 10-amino-CPT, 10-amino-5-propyl-CPT, 10-amino-7-ethyl-CPT, 10-amino-7-ethoxy-CPT, 10- methylamino-CPT, 10-ethylamino-5-methyl-CPT, 10-methylamino-7-ethoxy-CPT, 10-chloro-CPT, 10-chloro-5-methoxy-CPT, 10-chloro-7-acetoxy-CPT, 10-bromo-CPT, 10-bromo-5-methoxy-CPT, 10-bromo-7-ethyl-CPT, 7-ethyl-5,10-dihydroxy-CPT, 7-ethyl-10-hydroxy-5-methoxy-CPT and 7-acetoxy-10-hydroxy-5-methoxy-CPT.

In accordance with the present invention, there is also provided a process for the preparation of various 10-substituted camptothecin derivatives of the general formula (I).

In one embodiment of the process, 10-substituted camptothecin derivatives of the general formula:

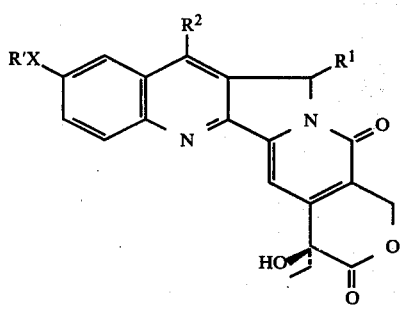

wherein $R^1$ is a hydrogen atom, an alkyl group, a hydroxyl group, an alkoxy group or an acyloxy group, $R^2$ is a hydrogen atom, an alkyl group, an aralkyl group, a hydroxymethyl group, a carboxymethyl group or an acyloxymethyl group, $R'$ is a hydrogen atom, an alkyl group or an acyl group and X is an oxygen atom or a sulfur atom, can be prepared by treating camptothecin or a 5- and/or 7-substituted camptothecin derivative of the general formula:

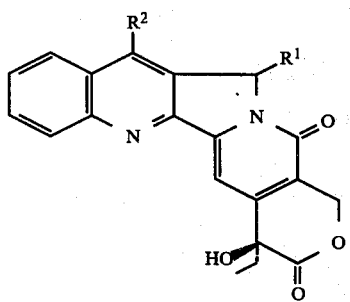

wherein $R^1$ and $R^2$ have the same meanings as given above, with a peroxidant in a liquid vehicle and then reacting the resultant camptothecin-1-oxide or 5- and/or 7-substituted camptothecin-1-oxide derivative with an active hydrogen-containing reagent of the general formula:

R'—XH   (III)

wherein R' and X have the same meanings as given above, in the presence of an acid under irradiation of UV-rays.

The 5- and/or 7-substituted camptothecin derivatives of the general formula (II) used as the starting material are known or can be prepared according to the known prior art processes.

In the first step, the starting camptothecin or 5- and/or 7-substituted camptothecin derivatives used are reacted in a liquid vehicle with a peroxidant to the corresponding-1-oxides (N-oxides). The peroxidant utilizable in the first step for N-oxidation of the ring B (pyridine ring) is selected from the group consisting of hydrogen peroxide, inorganic and organic peracids and salts thereof. Preferable examples of the peroxidant include hydrogen peroxide, peracetic acid, perbenzoic acid, m-chloroperbenzoic acid and a persulfate. The use of hydrogen peroxide in acetic acid is desirable as a higher yield of the N-oxide product is obtainable thereby. Illustrative of the liquid vehicle are, for example, glacial acetic acid, an aqueous acetic acid solution, hydrocarbons such as benzene and hexane, chlorinated hydrocarbons such as chloroform and methylene chloride, and ethers such as dioxane.

In an embodiment wherein hydrogen peroxide is used for N-oxidation, the operation itself is carried out in a manner similar to that described, for example, in Mosher et al., Org. Syn. 33, 79 (1953) or Ochiai et al., J. Pharm. Soc. Japan 71, 1385 (1951); the starting camptothecin derivative of the general formula (II) is suspended or dissolved in acetic acid and treated under agitation with hydrogen peroxide (usually about 30% in strength). The selection of a temperature range from 65° C. to 70° C. is adequate for this reaction. Although a theoretically needed amount of hydrogen peroxide is one mol per mol of the starting camptothecin derivative, the use of a larger excess (about 30 molar proportion) of hydrogen peroxide is preferable. Under such conditions, N-oxidation of the starting camptothecin derivative is completed normally within 4 hours.

In another embodiment wherein a peracid is used for N-oxidation, the operation itself is carried out in a manner similar to that described, for example, in Herz et al., J. Am. Chem. Soc. 76, 4184 (1954); the starting camptothecin derivative of the general formula (II) is treated, for example, with peracetic acid (usually 40% in concentration) and sodium acetate or with perbenzoic acid in benzene. It is possible to use m-chloroperbenzoic acid as the peroxidant in chloroform or ethylene chloride. It is also possible to use sodium persulfate under similar conditions.

The resultant N-oxide intermediate product can be isolated in a highly pure form by concentrating the reaction mixture under reduced pressure to a volume of about 1/5–1/10, diluting the concentrate with a large excess of ice water, collecting the resultant N-oxide precipitated as needle crystals by filtration, and drying the crystals under subatmospheric pressure.

In the second step, the intermediately formed N-oxide is dissolved in a solvent and treated with an active hydrogen-containing reagent of the general formula (III) in the presence of an acid under irradiation of UV-rays. Preferred as the solvent in this reaction are dioxane, acetonitrile, chloroform, methylene chloride, glyme, diglyme and a mixture of these. Illustrative of the active hydrogen-containing reagent of the general formula (III) are, for example, water, hydrogen sulfide, a monohydric alcohol such as methanol, ethanol, propanol or butanol, an organic acid such as acetic acid or propionic acid, and an alkylmercaptan such as methylmercaptan, ethylmercaptan or mercaptoacetic acid esters. Preferable examples of the acid to be present in the reaction system include mineral acids such as sulfuric acid and perchloric acid, organic sulfonic acids such as ethanesulfonic acid and p-toluenesulfonic acid, Lewis acids such as boron trifluoride-etherate, and organic carboxylic acids such as acetic acid and propionic acid. A good result can be obtained when the acid is used in an amount of 10–15 molar equivalents. The operation for irradiating the reaction mixture with UV-rays is performed according to a known conventional method. The irradiation time is usually between 15–100 minutes and a commercially available high voltage mercury lamp can be used as a source of UV-rays. In case acetic or propionic acid is used as the acid to be present in the reaction system, it also functions as a solvent.

According to the two-step reaction referred to above, the starting camptothecin or a 5- and/or 7-substituted derivative thereof is first converted into the corresponding N-oxide and then the grouping R'X— in the active hydrogen-containing reagent of the general formula (III) is introduced into the 10-position of camptothecin or a derivative thereof with simultaneous elimination of the oxygen atom in the 1-position under irradiation of UV-rays. The reaction mixture thus treated contains two kinds of product, one being a small amount of 1-deoxygenated product (the starting material) and the other being the end product carrying the substituent —XR' in its 10-position. These products can be separated by HPLC or column chromatography on silica gel and the recovered starting material can be used for the next batch. The end product can be purified, if necessary, by way of chromatography or the so-called recrystallization method.

In another embodiment of the process of this invention, 10-substituted camptothecin derivatives of the general formula:

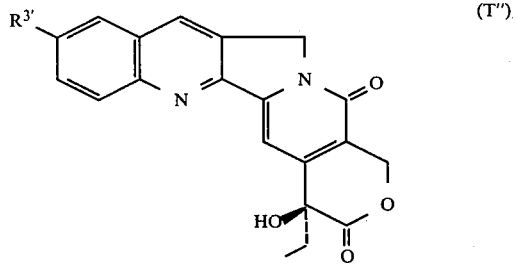

(T")

wherein $R^{3'}$ is a nitro group, an amino group, an alkylamino group, an acylamino group, a hydroxyl group or a halogen atom, can be prepared by catalytically hydrogenating camptothecin in a solvent under atmospheric pressure by the aid of a noble metal catalyst, treating the resultant 1,2,6,7-tetrahydrocamptothecin with an acylating agent to introduce the acyl group into the 1-position, treating the thus obtained 1-acyl-1,2,6,7-tetrahydrocamptothecin with a mixture of nitric acid and sulfuric acid, eliminating the 1-acyl group in the resultant 1-acyl-10-nitro-1,2,6,7-tetrahydrocamptothecin by hydrolysis and treating the resultant 10-nitro-1,2,6,7-tetrahydrocamptothecin with an oxidizing agent for dehydrogenation, and if desired, reducing the resultant 10-nitro-camptothecin or 10-nitro-1,2,6,7-tetrahydrocamptothecin prior to dehydrogenation to convert the nitro group into amino group, and then modifying the amino group by N-alkylation or N-acylation or by diazotization followed by hydrolysis or the Sandmeyer reaction, and if necessary, treating the resulting compound with an oxidizing agent for dehydrogenation.

In the first step for hydrogenating the ring B (the pyridine ring), camptothecin is catalytically hydrogenated at room temperature in a solvent such as acetic acid or dioxanehydrochloric acid under atmospheric pressure by the aid of a noble metal catalyst until the theoretical amount of hydrogen is absorbed. The hydrogenation reaction will be completed usually within 2 hours. Preferable examples of the noble metal hydrogenation catalyst include platinum black, platinum oxide, palladium black, and palladium oxide as such or in the form carried on carbon black. These catalysts are well known in the field of hydrogenation. The reaction mixture is then filtered to remove the catalyst, and the filtrate is concentrated. The residue is then dissolved and subjected to column chromatography on silica gel to purify the hydrogenated product. A small amount of unreacted camptothecin can be recovered by this purification treatment.

In the second step, the resultant 1,2,6,7-tetrahydrocamptothecin is treated with an acylating agent under the conditions known per se for acylation. Any of the known conventional acylating agents, for example, acids in reactive functional form can be used for this purpose. Illustrative of the acylating agent are acetic anhydride, acetyl halide or the like lower fatty acid anhydride or halide, benzoyl chloride or the like aromatic acid halide, and p-toluenesulfonyl halides or the like sulfonyl halides. An acid-binding agent for this acylation is preferably a tertiary amine or a weak inorganic base. The use of triethylamine or pyridine is desirable. By this acylation, 1-acylated 1,2,6,7-tetrahydrocamptothecin is obtained in a high yield (above 70%) with a small amount of unreacted starting material. As 1,2,6,7-tetrahydrocamptothecin has a hydroxyl group in the 20-position thereof, acylation of the 20-hydroxyl group also proceeds simultaneously with N-acylation of the 1-position. However, a 1,20-diacylated product can be used for the subsequent step as the acylated group will eventually be removed in the next step. In case of using acetic anhydride, the acylation reaction is completed by warming the reaction mixture (at 50°–80° C.) for 1–2 hours, although the condition may be varied according to the nature of the acylating agent. The resultant crude product is isolated by removing the excess acylating agent and the solvent under reduced pressure and may be purified, if desired, by way of column chromatography on silica gel.

In the third step for nitration, 1-N-acetyl-20-O-acetyl-1,2,6,7-tetrahydrocamptothecin obtaind in the second step is dissolved in concentrated sulfuric acid and treated with fuming nitric acid under cooling for 20–40 minutes. The crude product is isolated by diluting the reaction mixture with ice water, extracting the organic phase with an organic solvent and evaporating the solvent under reduced pressure, and may be purified by way of column chromatography on silica gel. Although a nitro group cannot be introduced into the 10-position of camptothecin by directly nitrating camptothecin itself under the same conditions as described above, a nitro group can selectively be introduced into the 10-position of camptothecin according to the process of this invention by once converting it into 1-aceyl-1,2,6,7-tetrahydrocamptothecin. The nitrated compound is then subjected to hydrolysis under an acidic or alkaline condition in a conventional manner to split off the acyl group. For this purpose, the nitrated compound is refluxed for several hours in dilute mineral acid or a weak alkaline solution. The reaction mixture is then diluted with water or ice water and the water-insoluble deacylated product is extracted with a water-immiscible solvent and isolated by evaporating the solvent under reduced pressure. The hydrolyzed compound is then subjected to oxidation for dehydrogenation of the hydrogenated ring to the original aromatic ring. This oxidation itself is carried out in a known conventional manner using DDQ, air, nitric acid or the like oxidizing agent. The use of DDQ is preferable and the reaction can be conducted by refluxing the mixture for about one hour. The end product can be isolated in a pure form by concentrating the reaction mixture under reduced pressure, extracting the residue with a solvent and evaporating the solvent under reduced pressure.

10-Nitrocamptothecin thus obtained can further be modified, if desired, to convert the nitro group into other functional substituents. If necessary, such modification of the nitro group may be carried out for the intermediately formed 1-acetyl-10-nitro-1,2,6,7-tetrahydrocamptothecin or 10-nitro-1,2,6,7-tetrahydrocamptothecin prior to hydrolysis followed by oxidation (dehydrogenation of the saturated ring) or oxidation, respectively.

In order to obtain the product of the general formula (I') wherein $R^{3'}$ is an amino group, 10-nitrocamptothecin, its tetrahydro derivative or its 1-acyl-tetrahydro derivative is subjected to a conventional reductive reaction contemplated for reducing a nitro group to an amino group. Usually, Clemensen' reduction method (a combination of dilute mineral acid and tin, iron or zinc) or a catalytic reduction method is used for this purpose. Advantageously, 10-nitrocamptothecin is dissolved in a solvent and hydrogenated at room temperature under atmospheric pressure in the presence of a small amount of platinum oxide. In this case, the desired 10-aminocamptothecin can be obtained by removing the catalyst from the reaction mixture by filtration and evaporating the solvent under reduced pressure.

10-Aminocamptothecin or its tetrahydro derivative thus obtained can further be modified in various ways. In one embodiment, 10-aminocamptothecin or its derivative is alkylated in a conventional manner with an N-alkylating agent. As an alternative method, 10-aminocamptothecin or its derivative may first be acylated with an alkanoyl halide or alkanoic anhydride and then the carbonyl group in the resultant 10-alkanoylaminocamptothecin may be reduced in a conventional manner.

In another embodiment, the 10-amino compound (10-aminocaptothecin or its tetrahydro derivative) is treated with a variety of acylating agents in accordance with a conventional method for acylating the free amino group to obtain 10-acylaminocamptothecin. For this purpose, various kinds of acylating agents such as acid anhydrides and acid halides of aliphatic, especially fatty acids with 1-18, preferably 1-8 carbon atoms, e.g. acetyl chloride, acetic anhydride, propionyl chloride, and butyric anhydride; of aromatic and heterocyclic acids, e.g. benzoyl chloride and nicotinoyl chloride; of aralkanoic acids, e.g. phenylacetyl chloride; and of aliphatic and aromatic sulfonic acid, e.g. ethanesulfonyl chloride and p-toluenesulfonyl chloride, come into question. The acylation can advantageously be carried out by treating 10-aminocamptothecin in a solvent with such an acylating agent in the presence of an acid-binding agent such as pyridine.

In still another embodiment, the 10-amino compound is treated with a nitrite in an aqueous acidic medium to form the corresponding diazonium salt, which is then hydrolyzed under heating to form 10-hydroxycamptothecin. The diazotization of the 10-amino compound can be carried out in a conventional manner by adding an aqueous solution of a nitrite slowly to an acidic solution of the 10-amino compound under stirring and ice cooling. After completion of the diazotization, the mixture is heated to cause hydrolysis of the 10-diazonium salt whereby the corresponding 10-hydroxy compound is obtained. Likewise, the 10-diazonium salt can be treated with methanol to cause methanolysis, thereby forming the 10-methoxy compound. 10-Hydroxycamptothecin, and 10-methoxy- and 10-acetoxy camptothecin, are already known as extracts from Camptotheca acuminata but could for the first time be synthesized from camptothecin by the present inventors.

In a further embodiment, the 10-diazonium salt derived from the corresponding 10-amino compound is treated in an acidic medium with cuprous halide according to the so-called Sandmeyer reaction to form the corresponding 10-halogeno compound. In the preparation of 10-chlorocamptothecin, for example, an ice-cooled solution of the 10-diazonium chloride is slowly added dropwise to a warm acidic solution of cuprous chloride. Likewise, 10-bromocamptothecin can be prepared from a combination of the 10-diazonium bromide and cuprous bromide.

The compounds of the general formula (I) and those prepared for the first time according to the process of this invention can further be modified, if desired, by converting their 5-, 7- and/or 10-substituent into another substituent according to a method known per se. For example, the free hydroxyl group in any of the 5-, 7- and 10-positions of the end product may be acylated or alkylated in a conventional manner to form modified compounds which are still involved in the compounds represented by the general formula (I).

The end products obtained according to the process of this invention can be used as such without further purification as active ingredients for medicaments or as valuable intermediate products for preparing other useful products.

Thus, the present invention is of particular significance in developing 10-substituted camptothecin derivatives as a new class of camptothecin derivatives which are useful as anti-tumor agents possessing anti-tumor activity with reduced toxicity and also as intermediate products for preparing other useful products as well as a new process for preparing these camptothecin derivatives in simple industrially advantageous operations.

The present invention will now be illustrated in more detail by way of examples. In these examples, the percentages are by weight unless otherwise indicated.

EXAMPLE 1

(A) Preparation of camptothecin-1-oxide

Camptothecin (1.04 g, 3 m-mol) is suspended in acetic acid (100 ml). To this suspension is added 30% hydrogen peroxide (15 ml), and the mixture is stirred for 3 hours at 60°–70° C. The resultant reaction mixture is concentrated under reduced pressure to a volume of about 35 ml and the concentrate is then poured into ice water (500 ml). The precipitated yellowish orange needle crystals are collected by filtration, washed with water and then with methanol and dried under reduced pressure whereby 866 mg (yield: 90.6%) of camptothecin-1-oxide is obtained. M.P. 254° C. (dec.)

(B) Preparation of 10-[(carboethoxymethyl)thio]camptothecin

Camptothecin-1-oxide (75 mg, 0.206 m-mol) obtained in the preceding (A) is dissolved in ethanol-free chloroform (50 ml) and dioxane (50 ml). To this solution are added boron trifluoride (50 μl) and ethyl thioglycolate (5 g), and the mixture is subjected to irradiation of a light beam for 40 minutes. The reaction mixture is concentrated under reduced pressure. Water (100 ml) is then added to the concentrate and the mixture is extracted with chloroform (100 ml×3). The chloroform phase is dried over magnesium sulfate, filtered and evaporated until dryness under reduced pressure. The residue is decolorized with silica gel (5 g) and subjected to purification by way of high pressure liquid chromatography (Richrosorb SI-60 column, 10% acetone-chloroform) whereby 20 mg (20.8%) of the objective compound is obtained together with 22 mg of camptothecin. Yellow needle crystals, M.P. 228°–231° C. (dec.) [chloroform-n-hexane]

NMR (in CDCl$_3$): 1.04 (3H, t, J=7.8 Hz), 1.25 (3H, t, J=7.3 HZ), 1.90 (2H, q, J=7.8 HZ), 3.81 (2H, s), 4.21 (2H, q, J=7.3 Hz), 5.28 (1H, d, J=16.6 Hz), 5.27 (2H, s), 5.75 (2H, d, J=16.6 Hz), 7.64 (1H, s), 7.70 (2H, m), 8.17 (1H, d, J=9 Hz), 8.26 (1H, br s)

MS: m/e 466 [M+] (C$_{24}$H$_{22}$N$_2$O$_6$S=466)

EXAMPLE 2

Preparation of 10-methoxycamptothecin

Camptothecin-1-oxide (75 mg, 0.206 m-mol) obtained in the preceding Example 1(A) is dissolved in methanol (50 ml) and dioxane (50 ml). To this solution is added conc. sulfuric acid (0.1 ml), and the mixture is subjected to irradiation of a light beam (high voltage mercury lamp, 250 W) for 25 minutes. The reaction mixture is concentrated under reduced pressure, diluted with water (100 ml) and extracted with chloroform (100 ml×3). The chloroform phase is dried over magnesium sulfate, filtered and evaporated under reduced pressure until dryness. To the residue are added acetic anhydride (0.5 ml) and pyridine (1 ml), and the mixture is stirred for 1.5 hours at 60°–70° C. The reaction mixture is evaporated until dryness under reduced pressure. The residue is decolorized with silica gel (5 g) and subjected to high pressure liquid chromatography (HPLC) using Richrosorb SI-60 column, 4% acetone-chloroform whereby 20-O-acetylcamptothecin (7 mg) and 20-O-acetyl-10-methoxycamptothecin (37 mg, m/e 420[M+] C$_{23}$H$_{20}$N$_2$O$_6$=420) are obtained. The latter compound is dissolved in conc. hydrochloric acid (2 ml) and methanol (1 ml) and the solution is stirred for 16 hours at room temperature. The reaction mixture is diluted with water (200 ml) and extracted with chloroform (200 ml). The chloroform phase is dried with magnesium sulfate, filtered and evaporated until dryness under reduced pressure whereby 28 mg (37.8%) of 10-methoxycamptothecin is obtained. M.P. 252°–254° C. (the value reported in the literature: m.p. 254°–255° C.). This compound is identified with a standard substance isolated from Camptotheca acuminata Nyssaceae, by way of HPLC and IR absorption spectra.

EXAMPLE 3

Preparation of 10-hydroxycamptothecin

Camptothecin-1-oxide (500 mg, 1.37 m-mol) obtained in the preceding Example 1(A) is dissolved in dioxane-acetonitrile-water (5:4:1, 500 ml). To this solution is added conc. sulfuric acid (1 ml), and the mixture is subjected to irradiation of a light beam for 90 minutes. The reaction mixture is concentrated under reduced pressure and diluted with water (1 l). The precipitate is collected by filtration and dried, and the resultant crude crystals are washed with methanol and purified by way of column chromatography on silica gel whereby 441 mg (yield: 88.2%) of 10-hydroxycamptothecin is obtained. This compound is identified with a standard substance isolated from Camptotheca acuminata Nyssaceae, by way of various spectral data.

EXAMPLE 4

Preparation of 10-acetoxycamptothecin

Camptothecin-1-oxide (75 mg, 0.206 m-mol) obtained in the preceding Example 1(A) is dissolved in acetic acid (100 ml) and the solution is subjected to irradiation of a light beam for 45 minutes. The reaction mixture is evaporated until dryness under reduced pressure and the residue is decolorized with silica gel (5 g) and purified by way of HPLC (Richrosorb SI-60 column, 10% acetone-chloroform) whereby 26 mg (yield: 31.1%) of 10-acetoxycamptothecin is obtained as light yellowish white crystals together with 27.5 mg of camptothecin. The former compound is identical in HPLC and various spectral data with a standard substance obtained by treating 10-hydroxycamptothecin isolated from Camptotheca acuminata Nyssaceae with acetic anhydride in pyridine.

EXAMPLE 5

(A) Preparation of 5-methylcamptothecin-1-oxide

5-Methylcamptothecin (362 mg, 1 m-mol) is dissolved in acetic acid (25 ml). To this solution is added 30% hydrogen peroxide (2.5 ml, 0.0245 mol), and the mixture is warmed for 3 hours at 65°–70° C. The reaction mixture is concentrated under reduced pressure to a volume of about one fifth and diluted with ice water (250 ml). The precipitated yellowish orange needle crystals are collected by filtration and dried at 60° C. for 6 hours under reduced pessure whereby 234 mg (yield: 62.0%) of 5-methylcamptothecin-1-oxide is obtained. M.P. 226° C.- (dec.).

MS: m/e 378 [M+] (C$_{21}$H$_{18}$N$_2$O$_5$=378)

(B) Preparation of 10-hydroxy-5-methylcamptothecin

5-Methylcamptothecin-1-oxide (27 mg, 0.0714 m-mol) obtained in the preceding (A) is dissolved in acetonitrile (20 ml)-dioxane (25 ml)-water (5 ml). To this solution is added conc. sulfuric acid (50 μl), and the mixture is subjected to irradiation of a light beam for 30 minutes. The reaction mixture is concentrated under reduced pressure and diluted with water (50 ml). The insoluble matter is collected by filtration, dried and purified by column chromatography on silica gel (2% methanol-chloroform) whereby 11 mg (yield: 50.6%) of the objective end product is obtained as light yellowish white crystals together with 5 mg of 5-methylcamptothecin.

NMR (in DMSO-d$_6$)δ: 0.87 (3H, t, J=7 Hz), 1.77 (3H, br d, J=6 Hz, C$_5$—CH$_3$), 1.84 (2H, q, J=7 Hz), 5.36 (2H, br s, C$_{17}$—H$_2$), 5.60 (1H, m, C$_5$—H), 6.43 (1H, br s, D$_2$O-exchangeable), 7.07 (2H, m, C$_9$—H and C$_{14}$—H), 7.14 (1H, d×d, J=9 Hz, 2 Hz, C$_{11}$—H), 7.84 (1H, d, J=9 Hz, C$_{12}$—H), 8.41 (1H, br s, C$_7$—H), 10.34 (1H, s, D$_2$O-exchangeable)

MS: m/e 378 [M+] ($C_{21}H_{18}N_2O_5=378$)

EXAMPLE 6

(A) Preparation of 5-methoxycamptothecin-1-oxide

5-Methoxycamptothecin (190 mg, 0.5 m-mol) is dissolved in acetic acid (15 ml). To this solution is added 30% hydrogen peroxide (1.25 ml, 0.0125 mol), and the mixture is stirred for 3 hours at 65°–70° C. The reaction mixture is concentrated under reduced pressure to a volume of about one fourth and diluted with ice water (200 ml). The precipitated yellowish orange needle crystals are collected by filtration and then dried under reduced pressure for 6 hours at 60° C. whereby 145 mg (yield: 73.6%) of 5-methoxycamptothecin-1-oxide with 7 mg of 5-methoxycamptothecin is obtained. M.P. 208° C.- (dec.)

NMR (in $CDCl_3$): 1.03 (3H, t, J=7 Hz), 1.92 (2H, q, J=7 Hz), 3.51, 3.66 (1.5H×2, s, s), 5.30 (1H, d, J=16 Hz), 5.59 (1H, d, J=16 Hz), 6.73, 6.85 (0.5H×2, s, s), 7.72–8.01 (4H, m), 8.24 (1H, s), 8.76 (1H, m),

MS: m/e 394 [M+] ($C_{21}H_{18}N_2O_6=394$)

(B) Preparation of 10-hydroxy-5-methoxycamptothecin

5-Methoxycamptothecin-1-oxide (98 mg, 0.248 m-mol) is dissolved in acetonitrile (50 ml)-dioxane (50 ml)-water (5 ml). To this solution is added conc. sulfuric acid (100 μl), and the mixture is subjected to irradiation of a light beam for 30 minutes. The reaction mixture is concentrated under reduced pressure and diluted with water (100 ml). The insoluble matter is collected by filtration, dried and purified by column chromatography on silica gel (2% methanol-chloroform) whereby 23.5 mg (yield: 26.1%) of the objective end product is obtained together with 5-methoxycaptothecin.

NMR (in DMSO-$d_6$)δ: 0.87 (3H, t, J=7 Hz), 1.83 (2H, q, J=7 Hz), 3.46, 3.54 (1.5H×2, s, s, $C_5$—$OCH_3$), 5.39 (2H, br s, $C_{17}$—H), 6.28 (1H, br s, $D_2O$-exchangeable), 6.80, 6.86 (0.5H×2, s, s, $C_5$—H), 7.02 (1H, d, J=2 Hz, $C_9$—H), 7.21 (1H, br, s, $C_{14}$—H), 7.25 (1H, d, d, J=9 Hz, 2 Hz, $C_{11}$—H), 7.90 (1H, d, J=9 Hz, $C_{12}$—H), 8.48 (1H, br s, $C_7$—H), 10.36 (1H, s, $D_2O$-exchangeable)

MS: m/e 394 [M+] ($C_{21}H_{18}N_2O_6=394$)

EXAMPLE 7

(A) Preparation of 7-ethylcamptothecin-1-oxide

7-Ethylcamptothecin (1.00 g, 2.65 m-mol) is dissolved in acetic acid (300 ml). To this solution is added 30% hydrogen peroxide (7.5 ml, 0.0736 mol), and the mixture is stirred for 3 hours at 65°–70° C. The reaction mixture is concentrated under reduced pressure to a volume of about one fourth and diluted with ice water (500 ml). The precipitated yellowish orange needle crystals are collected by filtration and dried for 6 hours at 60° C. under reduced pressure whereby 808 mg (yield: 77.7%) of 7-ethylcamptothecin-1-oxide is obtained. M.P. 255° C.- (dec.)

NMR (in DMSO-$d_6$): 0.87 (3H, t, J=7 Hz), 1.28 (3H, t, J=7 Hz), 1.84 (2H, q, J=7 Hz), 3.10 (2H, q, J=7 Hz), 5.26 (2H, s), 5.36 (2H, s), 6.24 (1H, s, $D_2O$-exchangeable), 7.80 (3H, m), 8.10 (1H, s), 8.35 (1H, m)

MS: m/e 392 [M+] ($C_{22}H_{20}N_2O_5=392$)

(B) Preparation of 7-ethyl-10-hydroxycamptothecin

7-Ethylcamptothecin-1-oxide (100 mg, 0.255 m-mol) is dissolved in acetonitrile (65 ml)-dioxane (30 ml)-water (5 ml). To this solution is added conc. sulfuric acid (0.1 ml), and the mixture is subjected to irradiation of a light beam for 25 minutes. The reaction mixture is concentrated under reduced pressure, diluted with water (100 ml) and extracted with chloroform (100 ml×3). The chloroform phase is dried over magnesium sulfate, filtered and evaporated under reduced pressure until dryness. The residue is purified by column chromatography on silica gel (2% methanolchloroform) whereby 43 mg (yield: 49.1%) of the objective end product is obtained as light yellowish white crystals together with 12 mg of 7-ethylcamptothecin. M.P. 231° C.- (dec.) [EtOH]

NMR (in $CDCl_3$)δ: 0.98 (3H, t, J=7 Hz), 1.38 (3H, t, J=7 Hz), 1.90 (2H, q, J=7 Hz), 3.08 (2H, q, J=7 Hz), 5.17 (2H, s), 5.23 (1H, d, J=16 Hz), 5.54 (1H, d, J=16 Hz), 7.34 (2H, m), 7.39 (1H, s), 7.92 (1H, d, J=9 Hz)

MS: m/e 392 [M+] ($C_{22}H_{20}N_2O_5=392$)

EXAMPLE 8

Preparation of 7-ethyl-10-methoxycamptothecin

7-Ethylcamptothecin-1-oxide (100 mg, 0.255 m-mol) obtained in the preceding Example 7(A) is dissolved in methanol (50 ml)-dioxane (50 ml). To this solution is added conc. sulfuric acid (0.1 ml) and the mixture is subjected to irradiation of a light beam for 30 minutes. The reaction mixture is concentrated under reduced pressure, diluted with water (100 ml) and extracted with chloroform (100 ml×3). The chloroform phase is dried with magnesium sulfate, filtered and evaporated until dryness under reduced pressure. The residue is decolorized with silica gel (5 g) and purified by HPLC (Richrosorb SI-60 column, 10% acetone-chloroform) whereby 27 mg (yield: 33.2%) of the objective end product is obtained together with 18 mg of 7-ethylcamptothecin. Light yellowish white needle crystals with M.P. 261° C.- (dec.) [n-hexane-chloroform]

NMR (in $CDCl_3$)δ: 1.28 (3H, t, J=7 Hz), 1.49 (3H, t, J=7 Hz), 1.97 (2H, q, J=7 Hz), 3.24 (2H, q, J=7 Hz), 4.30 (3H, s), 5.27 (2H, s), 5.25 (1H, d, J=16 Hz), 5.70 (1H, d, J=16 Hz), 7.20 (1H, d, J=3 Hz), 7.47 (1H, d×d, J=9 Hz, 3 Hz), 7.72 (1H, s), 8.53 (1H, d, J=9 Hz)

MS: m/e 406 [M+] ($C_{23}H_{22}N_2O_5=406$)

EXAMPLE 9

(A) Preparation of 7-propylcamptothecin-1-oxide

7-Propylcamptothecin (390 mg, 1 m-mol) is dissolved in acetic acid (55 ml). To this solution is added 30% hydrogen peroxide (3 ml, 0.0294 m-mol), and the mixture is stirred for 4 hours at 65°–70° C. The reaction mixture is concentrated under reduced pressure to a volume of about 10 ml and diluted with ice water (250 ml). The precipitated yellowish orange needle crystals are collected by filtration and dried for 6 hours at 60° C. under reduced pressure whereby 278 mg (yield: 68.4%) of 7-propylcamptothecin-1-oxide is obtained. M.P. 238° C.- (dec.)

MS: m/e 406 [M+] ($C_{23}H_{22}N_2O_5=406$)

(B) Preparation of 10-hydroxy-7-propylcamptothecin

7-Propylcamptothecin-1-oxide (200 mg, 0.493 m-mol) obtained in the preceding (A) is dissolved in dioxane (60 ml)-acetonitrile (20 ml)-water (5 ml). To this solution is added conc. sulfuric acid (100 μl), and the mixture is subjected to irradiation of a light beam for 30 minutes. The reaction mixture is concentrated under reduced pressure and diluted with water (100 ml). The insoluble matter is collected by filtration, dried and purified by column chromatography on silica gel (2% methanolchloroform) whereby the objective end product (121 mg, yield: 60.5%) is obtained together with 11 mg of 7-propylcamptothecin. Light yellowish white needle crystals with M.P. 237° C.- (dec.) [toluene]

NMR (in DMSO-d$_6$)δ: 0.89 (3H, t, J=7 Hz), 1.06 (3H, t, J=7 Hz), 1.60–1.90 (5H, m), 3.00 (2H, t, J=7 Hz), 5.24 (2H, s), 5.40 (2H, s), 6.24 (1H, s, D$_2$O-exchangeable), 7.35 (1H, s), 7.30 (2H, m), 7.99 (1H, d, J=9 Hz)

MS: m/e 406 [M+] (C$_{23}$H$_{22}$N$_2$O$_5$=406)

EXAMPLE 10

(A) Preparation of 7-benzylcamptothecin-1-oxide

7-Benzylcamptothecin (250 mg, 0.570 m-mol) is dissolved in acetic acid (50 ml). To this solution is added 30% hydrogen peroxide (2 ml, 0.0196 mol), and the mixture is stirred for 3 hours at 65°–70° C. The reaction mixture is concentrated under reduced pressure to a volume of about 10 ml and then diluted with ice water (250 ml). The precipitated yellowish orange needle crystals are collected by filtration and dried for 6 hours at 60° C. under reduced pressure whereby 164 mg (yield: 63.5%) of 7-benzylcamptothecin-1-oxide is obtained. M.P. 220° C.-(dec.)

NMR (in CDCl$_3$): 1.09 (3H, t, J=7.5 Hz), 1.87 (2H, q, J=7.5 Hz), 4.48 (2H, s), 5.16 (2H, s), 5.20 (1H, d, J=16 Hz), 5.64 (1H, s, J=16 Hz), 7.05–8.12 (8H, m), 8.32 (1H, s), 8.80 (1H, m)

MS: m/e 454 [M+] (C$_{27}$H$_{22}$N$_2$O$_5$=454)

(B) Preparation of 10-acetoxy-7-benzylcamptothecin

7-Benzylcamptothecin-1-oxide (100 mg, 0.22 m-mol) obtained in the preceding (A) is dissolved in acetic acid (100 ml) and the solution is subjected to irradiation of a light beam for one hour. The reaction mixture is evaporated under reduced pressure until dryness. The residue is decolorized with silica gel (5 g) and purified by HPLC (Richrosorb SI-60 column, 4% acetone-chloroform) whereby 28 mg (yield: 29.9%) of the objective end product is obtained together with 14 mg of 7-benzylcamptothecin. The product is recrystallized from n-hexane-chloroform to afford light yellowish white needle crystals. M.P. 226° C.- (dec.)

NMR (in CDCl$_3$)δ: 1.03 (3H, t, J=7.3 Hz), 1.85 (2H, q, J=7.3 Hz), 2.37 (3H, s), 4.52 (2H, s), 5.11 (2H, s), 5.26 (1H, d, J=16 Hz), 5.73 (1H, d, J=16 Hz), 7.10 (5H, m), 7.53 (1H, d×d, J=9 Hz, 3 Hz), 7.65 (1H, s), 7.89 (1H, d, J=3 Hz), 8.27 (1H, d, J=9 Hz)

MS: m/e 496 [M+] (C$_{29}$H$_{24}$N$_2$O$_6$=496)

EXAMPLE 11

(A) Preparation of 7-acetoxymethylcamptothecin-1-oxide

7-Acetoxymethylcamptothecin (1.0 g, 2.38 m-mol) is dissolved in acetic acid (150 ml). To this solution is added 30% hydrogen peroxide (10 ml, 0.0981 mol), and the mixture is stirred for 3.5 hours at 65°–70° C. The reaction mixture is concentrated under reduced pressure to a volume of about 50 ml, diluted with ice water (350 ml) and extracted with chloroform (300 ml×3). The chloroform phase is washed with a 7% aqueous solution of sodium hydrogen carbonate, dried over magnesium sulfate and dried until dryness under reduced pressure. The residue is purified by reprecipitation with chloroform-n-hexane whereby 679 mg (yield: 65.9%) of 7-acetoxymethylcamptothecin-1-oxide is obtained as yellow needle crystals. M.P. 250° C.- (dec.)

NMR (in DMSO-d$_6$): 0.87 (3H, t, J=7 Hz), 1.83 (2H, q, J=7 Hz), 2.05 (3H, s), 5.42 (4H, br s), 5.61 (2H, s), 6.42 (1H, s, D$_2$O-exchangeable), 7.80 (2H, m), 7.91 (1H, s), 8.20 (1H, m), 8.63 (1H, m)

MS: m/e 436 [M+] (C$_{23}$H$_{20}$N$_2$O$_7$=436)

(B) Preparation of 7-acetoxymethyl-10-hydroxycamptothecin

7-Acetoxymethylcamptothecin-1-oxide (75 mg, 0.172 m-mol) obtained in the preceding (A) is dissolved in dioxane (40 ml)-acetonitrile (50 ml)-water (10 ml). To this solution is added conc. sulfuric acid (0.1 ml), and the mixture is subjected to irradiation of a light beam for 45 minutes. The reaction mixture is concentrated under reduced pressure to about half a volume, diluted with water (100 ml) and extracted with chloroform (200 ml×2). The chloroform phase is dried over magnesium sulfate, filtered and evaporated until dryness under reduced pressure. The pressure is separated by way of column chromatography on silica gel (2% methanol-chloroform) whereby 24 mg (yield: 32%) of the objective end product is obtained together with 7-acetoxymethylcamptothecin (22 mg). Light yellowish white needle crystals, M.P. 257° C. (dec.) [n-hexane-chloroform]

NMR (in DMSO-d$_6$)δ: 0.98 (3H, t, J=7 Hz), 1.38 (3H, t, J=7 Hz), 1.90 (2H, q, J=7 Hz), 3.08 (2H, q, J=7 Hz), 5.17 (2H, s), 5.23 (2H, s), 5.54 (2H, s), 6.34 (1H, br, D$_2$O-exchangeable), 7.34 (2H, m), 7.39 (1H, s), 7.92 (1H, d, J=9 Hz)

MS: m/e 436 [M+] (C$_{23}$H$_{20}$N$_2$O$_7$=436)

EXAMPLE 12

(A) Preparation of 7-hydroxymethylcamptothecin-1-oxide

7-Hydroxymethylcamptothecin (300 mg, 0.794 m-mol) is suspended in glacial acetic acid (70 ml). To this suspension is added 30% hydrogen peroxide (30 ml), and the mixture is stirred for one hour at 70°–80° C. 30% Hydrogen peroxide (20 ml) is added and the mixture is further stirred for 1.5 hours at 70°–80° C. The reaction mixture is concentrated under reduced pressure to a volume of 40 ml. Ice water (60 ml) is added to the concentrate and the mixture is allowed to stand for 12 hours. The precipitated yellow crystals are collected by filtration and dried under reduced pressure whereby 142 mg (yield: 45.4%) of the objective compound is obtained as yellow needle crystals. M.P. 255°–260° C. (dec.)

IR $\nu_{max}^{KBr}$ cm$^{-1}$: 3400, 2940, 1755, 1650, 1600, 1460, 1160 1100, 765

(B) Preparation of 7-hydroxymethyl-10-hydroxycamptothecin

7-Hydroxymethylcamptothecin-1-oxide (50 mg, 0.127 m-mol) obtained in the preceding (A) is dissolved in a solvent mixture of dioxane (40 ml), acetonitrile (40 ml) and water (10 ml). To this solution is added conc. sulfuric acid (3 drops), and the mixture is subjected to irradiation of a light beam for 10 minutes. The reaction mixture is concentrated under reduced pressure and water (20 ml) is added to the residue. The insoluble matter is collected by filtration and dried to obtain 40 mg (80%) of the objective compound, which is purified by chromatography on silica gel. M.P. 260°–263° C. (dec.)

IR $\nu_{max}^{KBr}$ cm$^{-1}$: 3400, 2980, 1735, 1650, 1590, 1240, 1160, 1100, 800, 775

EXAMPLE 13

(A) Preparation of 1,2,6,7-tetrahydrocamptothecin

Camptothecin (500 mg, 1.43 m-mol) is suspended in acetic acid (100 ml). Platinum oxide (100 mg) is added to the suspension and the mixture is subjected to catalytic reduction (1.5 hours, absorption of about 140 ml of hydrogen) at room temperature under atmospheric pressure. After removing the catalyst by filtration, the reaction mixture is evaporated until dryness under reduced pressure. The residue is taken up in chloroform (200 ml) and washed with a 5% aqueous solution of sodium hydrogen carbonate (100 ml) and then with a saturated solution of sodium chloride (100 ml). The chloroform phase is dried over magnesium sulfate, filtered and evaporated under reduced pressure until dryness. The residue is purified by column chromatography (chloroform) on silica gel (20 g) whereby 285 mg (conversion rate: 56.3%; yield: 76.7%) of the objective compound is obtained as yellowish white crystals. Unreacted starting materials (113 mg in crude state) is recovered. M.P. (dec.) 240°–242° C. (from methanol)

IR $\nu_{max}^{KBr}$ cm$^{-1}$: 3470, 1745, 1645, 1565, 1495, 1165, 1030

(B) Preparation of 1,20-O-diacetyl-1,2,6,7-tetrahydrocamptothecin

Camptothecin (500 mg, 1.43 m-mol) is suspended in acetic acid (100 ml). Platinum oxide (100 mg) is added to the suspension and the mixture is subjected to catalytic reduction (1.5 hours at room temperature, absorption of about 140 ml of hydrogen) under atmospheric pressure. After removing the catalyst by filtration, the reaction mixture is evaporated until dryness under reduced pressure. The residue is taken up in pyridine (5 ml) and acetic anhydride (1 ml) is added. The mixture is warmed at 60°–65° C. for 1.5 hours and the reaction mixture is evaporated until dryness under reduced pressure. The residue is purified by column chromatography on silica gel (2% acetone-chloroform) whereby 349 mg (yield: 76.7%) of the objective compound is obtained and 149 mg of crude 20-O-acetylcamptothecin is recovered. Colorless needle crystals, M.P. <280° C. (from $C_6H_6$).

NMR (in CDCl$_3$)δ: 0.78 (3H, t, J=7 Hz, —CH$_2$C$\underline{H_3}$), 2.18 (2H, m, —C$\underline{H_2}$CH$_3$), 2.20 (6H, s, 20—O—COC$\underline{H_3}$ +N—1—COC$\underline{H_3}$), 2.80 (2H, br m, C—7—$\underline{H_2}$), 3.50 (2H, br m, C—5—$\underline{H_2}$), 4.10 (1H, m, C—6—$\underline{H}$), 5.02, 5.38 (1H, 1H, d×d, $\overline{J}$=17 Hz, C—17—$\underline{H_2}$), 7.20 (1H, s, C—14—$\underline{H}$), 7.24 (1H, m, C—2—$\underline{H}$), 7.69 (1H, m), 8.10 (3H, m)

MS: m/e 432 [M+] $C_{24}H_{24}N_2O_6$=432

(C) Preparation of 1-acetyl-10-nitro-1,2,6,7-tetrahydrocamptothecin

Camptothecin (500 mg, 1.44 m-mol) is suspended in a solvent mixture of glacial acetic acid (50 ml) and dioxane (50 ml). Platinum oxide (100 mg) is added to the suspension and the mixture is subjected to catalytic reduction at room temperature under atmospheric pressure for one hour. The catalyst is removed by filtration and the solvents are removed by distillation under reduced pressure. The residue is dissolved in chloroform (200 ml) and the solution is washed with a 5% aqueous solution of sodium hydrogen carbonate (50 ml). The chloroform phase is separated, dried over MgSO$_4$ and distilled under reduced pressure to remove the solvent. The above operation is repeated 6 times and the resultant 6 lots of products are blended with celite and then subjected to column chromatography on silica gel (eluent:ethyl acetate) whereby 1,2,6,7-tetrahydrocamptothecin is obtained. To this compound are added 5 ml of pyridine and 5 ml of acetic anhydride, and the mixture is warmed at 60° C. for one hour. The pyridine and the acetic anhydride are eliminated by distillation under reduced pressure and the residue is taken up in chloroform (300 ml) and washed with a 5% aqueous solution of hydrochloric acid and then with a 5% aqueous solution of sodium hydrogen carbonate. The chloroform phase is dried over MgSO$_4$ and the chloroform is removed by distillation under reduced pressure whereby 1-acetyl-20-O-acetyl-1,2,6,7-tetrahydrocamptothecin is obtained. This compound is dissolved in 50 ml of conc. sulfuric acid. Fuming nitric acid (0.9 ml) is added to the solution under ice cooling and the mixture is stirred for 30 minutes and poured into ice water (about 300 ml). The mixture is extracted with chloroform (200 ml×3) and the chloroform extract is dried with MgSO$_4$. The chloroform is removed by distillation under subatmospheric pressure and the residue is blended with celite and subjected to column chromatography on silica gel (eluent: 1% MeOH-CHCl$_3$) whereby 1.75 g (yield: 46.2% from camptothecin) of 1-acetyl-10-nitro-1,2,6,7-tetrahydrocamptothecin is obtained. Light yellowish white needle crystals, M.P. (with decomp.) 271°–273° C. (from AcOEt)

NMR (in DMSO-d$_6$)δ: 0.63 (3H, t, J=7 Hz, —CH$_2$C$\underline{H_3}$), 1.63 (2H, q, J=7 Hz, —C$\underline{H_2}$CH$_3$), 2.23 (3H, s, $\overline{N}$—1—COC$\underline{H_3}$), 2.8–3.0 (2H, br, m), 3.4–3.8 (3H, br, m), 4.0–4.2 (1$\overline{H}$, br, m), 5.10 (2H, s, C—17—H), 6.26 (1H, s, C—20—OH), 6.43 (1H, s, C—14—H), 7.53 (1H, d, J=9 Hz, C—12—H), 8.03 (1H, d, d, J=9 Hz, 2 Hz, C—11—H), 8.22 (1H, d, J=2 Hz, C—9—H)

IR $\nu_{max}^{KBr}$ cm$^{-1}$: 3450, 1755, 1660, 1585, 1525, 1375, 1345, 1300, 1155

MS: m/e 439 [M+] $C_{22}H_{21}N_3O_7$=439

(D) Preparation of 10-nitro-1,2,6,7-tetrahydrocamptothecin

1-Acetyl-10-nitro-1,2,6,7-tetrahydrocamptothecin (500 mg, 1.14 m-mol) is dissolved in a 20% aqueous solution of sulfuric acid (30 ml) and the solution is boiled under reflux for 2 hours. The reaction mixture is diluted with ice water (200 ml) and extracted with chloroform (200 ml×3). The chloroform phase is dried over magnesium sulfate, filtered and evaporated until dryness under reduced pressure whereby 373 mg (yield: 82.3%) of the objective compound is obtained as yellow crystals. M.P. (with decomp.) 274°–275° C. (from CHCl$_3$)

IR $\nu_{max}^{KBr}$ cm$^{-1}$: 3480, 1785, 1655, 1610, 1585, 1510, 1315, 1290, 1260

MS: m/e 397 [M+] $C_{20}H_{19}N_3O_6$=397

(E) Preparation of 10-nitrocamptothecin

10-Nitro-1,2,6,7-tetrahydrocamptothecin (373 mg, 0.937 m-mol) is dissolved in dioxane (30 ml). To this solution is added DDQ (446 mg, 1.968 m-mol), and the mixture is boiled under reflux for one hour. The reaction mixture is evaporated until dryness under reduced pressure and the residue is taken up in chloroform (300 ml) and washed with water (200 ml×2). The chloroform phase is dried over magnesium sulfate, filtered and evaporated until dryness under reduced pressure whereby 340 mg (yield: 92.3%) of the objective compound is obtained as yellow crystals. M.P. (with decomp.) 243°–245° C. (from chloroform)

NMR (in DMSO-$d_6$)δ: 0.89 (3H, t, J=7 Hz, —CH$_2$CH$_3$), 1.87 (2H, q, J=7 Hz, —CH$_2$CH$_3$), 5.28 (2H, s, C—5—H), 5.42 (2H, s, C—17—H), 6.51 (1H, s, C—20—OH), 7.33 (1H, s, C—14—H), 7.83 (1H, d, d, J=9 Hz, 2 Hz, C—11—H), 8.16 (1H, d, J=9 Hz, C—12—H), 8.25 (1H, d, J=2 Hz, C—9—H), 8.64 (1H, s, C—7—H)

IR $\nu_{max}^{KBr}$cm$^{-1}$: 3430, 1742, 1656, 1618, 1592, 1530, 1342, 1158

MS: m/e 393 [M+] $C_{20}H_{15}N_3O_6$=393

EXAMPLE 14

Preparation of 10-aminocamptothecin

10-Nitrocamptothecin (108 mg, 0.275 m-mol) is dissolved in ethanol (30 ml) and dioxane (20 ml). To this solution is added platinum oxide (20 mg), and the mixture is subjected to catalytic reduction for 30 minutes at room temperature under normal pressure. The catalyst is removed by filtration and the reaction mixture is evaporated under reduced pressure until dryness whereby 96 mg (yield: 96.2%) of 10-aminocamptothecin is obtained as a yellowish brown solid.

NMR (in DMSO-$d_6$)δ: 0.88 (3H, t, J=7 Hz, —CH$_2$CH$_3$), 1.86 (2H, q, J=7 Hz, —CH$_2$CH$_3$), 5.17 (2H, s, C—5—H), 5.39 (2H, s, C—17—H), 6.90 (1H, d, J=2 Hz, C—9—H), 7.19 (1H, s, C—14—H), 7.26 (1H, d, d, J=9 Hz, 2 Hz, C—11—H), 7.84 (1H, d, J=9 Hz, C—12—H), 8.20 (1H, s, C—7—H)

MS: m/e 363 [M+] $C_{20}H_{17}N_3O_4$=363

EXAMPLE 15

Preparation of 10-hydroxycamptothecin

10-Aminocamptothecin (50 mg, 0.138 m-mol) is dissolved in a 10% aqueous solution of sulfuric acid (5 ml). To this solution in a salted ice bath is slowly added dropwise an aqueous solution of sodium nitrite (9.5 mg, 0.138 m-mol) with stirring. After the addition of sodium nitrite, the mixture is further stirred for 10 minutes in a salted ice bath. To the reaction mixture is added conc. sulfuric acid (1 ml), and the whole is boiled under reflux for 2 hours. The reaction mixture is diluted with ice water (200 ml) and chloroform (200 ml) is added. The mixture is shaken in a separating funnel and the resultant emulsion is filtered through celite. The chloroform phase containing camptothecin formed as a by-product by side reactions is dried over magnesium sulfate, filtered and evaporated until dryness under reduced pressure whereby camptothecin (8 mg) is recovered. On the other hand, a solid on the celite, which is insoluble in chloroform-water, is taken up in 20% MeOH-CHCl$_3$ (200 ml) and the solution is evaporated until dryness under reduced pressure whereby 28 mg (yield: 66.5%) of the objective compound is obtained as light yellow crystals. M.P. (with decomp.) 270°–272° C. (from pyridine-methanol)

NMR (in DMSO-$d_6$)δ: 0.88 (3H, t, J=7 Hz, —CH$_2$CH$_3$), 1.86 (2H, q, J=7 Hz, —CH$_2$CH$_3$), 5.22 (2H, s, C—5—H), 5.40 (2H, s, C—17—H), 6.47 (1H, s, C—20—CH), 7.2 (2H, m, C—9—H and C—14—H), 7.41 (1H, d, d, J=9 Hz, 2 Hz, C—11—H), 8.01 (1H, d, J=9 Hz, C—12—H), 8.43 (1H, s, C—7—H)

IR $\nu_{max}^{KBr}$νcm$^{-1}$: 3450, 1720, 1655, 1590, 1505, 1265

EXAMPLE 16

Preparation of 10-chlorocamptothecin

1-Acetyl-10-nitro-1,2,6,7-tetrahydrocamptothecin (439 mg, 1.00 m-mol) obtained in Example 13(C) is dissolved in ethanol (30 ml) and dioxane (20 ml). To this solution is added platinum oxide (60 mg), and the mixture is subjected to catalytic reduction for 30 minutes at room temperature under normal pressure. The catalyst is removed by filtration and the reaction mixture is evaporated until dryness under reduced pressure whereby 1-acetyl-10-amino-1,2,6,7-tetrahydrocamptothecin (MS: m/e 409 [M+] $C_{22}H_{23}N_3O_3$=409) is obtained. This compound is dissolved in 12% hydrochloric acid (8 ml). To this solution in a salted ice bath is slowly added dropwise an aqueous solution of sodium nitrite (104 mg, 1.5 m-mol) with stirring. After the addition of sodium nitrite, the mixture is further stirred for 15 minutes under cooling in the salted ice bath. This reaction mixture is added dropwise to a solution of cuprous chloride (521 mg, 5.00 m-mol) in 17% hydrochloric acid (10 ml) warmed at 60°–70° C. under agitation. After the addition, the mixture is further agitated for one hour at 60°–70° C. The reaction mixture is diluted with ice water (300 ml) and extracted with chloroform (200 ml×2). The chloroform phase is dried over magnesium sulfate, filtered and evaporated until dryness under reduced pressure whereby 1-acetyl-10-chloro-1,2,6,7-tetrahydrocamptothecin (MS: m/e 428 [M+], 430 [M+2] $C_{22}H_{21}N_2O_5Cl$=428.5) is obtained. This compound is dissolved in a 30% aqueous solution of sulfuric acid (20 ml) and the solution is boiled under reflux for 1.5 hours. The reaction mixture is diluted with ice water (200 ml) and extracted with chloroform (150 ml×3). The chloroform phase is dried over magnesium sulfate, filtered and evaporated until dryness under reduced pressure to obtain 10-chloro-1,2,6,7-tetrahydrocamptothecin. This compound is dissolved in dioxane (30 ml) and DDQ (288 mg, 0.634 m-mol) is then added to the solution. The mixture is boiled under reflux for 1.5 hours and then evaporated until dryness under reduced pressure. The residue is dissolved in chloroform (300 ml) and washed with water (100 ml×2). The chloroform phase is dried over magnesium sulfate, filtered and evaporated until dryness under reduced pressure whereby 184 mg (yield: 48.0% from 1-acetyl-10-nitro-1,2,6,7-tetrahydrocamptothecin) of the objective compound is obtained as white crystals.

This end product can also be prepared from 10-aminocamptothecin by a diazotization followed by substitution reaction with cuprous chloride (Sandmeyer reaction) in the same manner as described above.

M.P. (with decomp.) 279°–280° C. (from CHCl$_3$)

NMR (in DMSO-$d_6$)δ: 0.89 (3H, t, J=7 Hz, —CH$_2$CH$_3$), 1.87 (2H, q, J=7 Hz, —CH$_2$CH$_3$), 5.28 (2H, s, C—5—H), 5.42 (2H, s, C—17—H), 6.51 (1H, s, C—20—OH), 7.33 (1H, s, C—14—H), 7.83 (1H, d, d, J=9 Hz, 2 Hz, C—11—H), 8.16 (1H, d, J=9 Hz, C—12—H), 8.25 (1H, d, J=2 Hz, C—9—H), 8.64 (1H, s, C—7—H)

IR $_{max}^{KBr}$νcm$^{-1}$: 3400, 1745, 1650, 1585, 1490, 1225, 1155

MS: m/e 382 [M+], 384 [M+2] $C_{20}H_{15}N_2O_4Cl$=382

EXAMPLE 17

Preparation of 10-bromocamptothecin

1-Acetyl-10-nitro-1,2,6,7-tetrahydrocamptothecin (439 mg, 1.00 m-mol) obtained in Example 13(C) is dissolved in ethanol (30 ml) and dioxane (20 ml). To this solution is added platinum oxide (60 mg), and the mixture is subjected to catalytic reduction for 30 minutes at room temperature under normal pressure. The catalyst is filtered off and the reaction mixture is evaporated until dryness under reduced pressure whereby 1-acetyl-10-amino-1,2,6,7-tetrahydrocamptothecin (MS: m/e 409 [M+] $C_{22}H_{23}N_3O_5=409$) is obtained. This compound is dissolved in 24% hydrobromic acid (10 ml). To this solution in a salted ice bath is slowly added dropwise an aqueous solution of sodium nitrite (104 mg, 1.50 m-mol) with stirring. After the addition of sodium nitrite, the mixture is continuously stirred for 15 minutes under cooling in the salted ice bath. The reaction mixture is added dropwise to a solution of cuprous bromide (717 mg, 5.00 m-mol) in 24% hydrobromic acid (10 ml) warmed at 60°–70° C. under agitation. After the addition, the mixture is continuously agitated for one hour at 60°–70° C. The reaction mixture is diluted with ice water (200 ml) and extracted with chloroform (200 ml×3). The chloroform phase is dried over magnesium sulfate, filtered and evaporated until dryness under reduced pressure whereby 1-acetyl-10-bromo-1,2,6,7-tetrahydrocamptothecin (MS: m/e 472 [M+], 474 [M+2] $C_{22}H_{21}N_2O_5Br=473$) is obtained. This compound is dissolved in a 30% aqueous solution of sulfuric acid (20 ml) and the solution is boiled under reflux for one hour. The reaction liquid is diluted with ice water (200 ml) and extracted with chloroform (200 ml×3). The chloroform phase is dried with magnesium sulfate, filtered and evaporated to dryness. The residue is blended with celite and subjected to column chromatography on silica gel (eluent: 1% MeOH-CHCl₃) whereby 10-bromo-1,2,6,7-tetrahydrocamptothecin (MS: m/e 430 [M+], 432 [M+2] $C_{20}H_{19}N_2O_4Br=431$) is obtained. This compound is dissolved in dioxane (20 ml). To this solution is added DDQ (264 mg, 0.58 m-mol), and the mixture is boiled under reflux for 40 minutes. The reaction mixture is evaporated until dryness under reduced pressure and the residue is dissolved in chloroform (300 ml) and washed with water (200 ml×2). The chloroform phase is dried with magnesium sulfate, filtered and evaporated until dryness under reduced pressure. The residue is blended with celite and purified by column chromatography on silica gel (eluent: 1% pyridine-chloroform) whereby 155 mg (yield: 36.3% from 1-acetyl-10-nitro-1,2,6,7-tetrahydrocamptothecin) of the objective compound is obtained as white crystals.

This end product can also be prepared from 10-aminocamptothecin by diazotization followed by a substitution reaction with cuprous bromide in the same manner as described above.

M.P. (with decomp.) 273°–275° C. (from CHCl₃)

NMR (in DMSO-d₆)δ: 0.89 (3H, t, J=7 Hz, —CH₂CH₃), 1.87 (2H, q, J=7 Hz, —CH₂CH₃), 5.28 (2H, s, C—5—H), 5.41 (2H, s, C—17—H), 6.48 (1H, s, C—20—OH), 7.34 (1H, s, C—14—H), 7.93 (1H, d. d, J=9 Hz, 2Hz, C—11—H), 8.09 (1H, d, J=9 Hz, C—1-2—H), 8.41 (1H, d, J=2 Hz), C—9—H), 8.63 (1H, s, C—7—H)

$IR_{max}^{KBr}$ νcm⁻¹: 3400, 1750, 1655, 1590, 1225, 1160

MS: m/e 426 [M+], 428 [M+2] $C_{20}H_{15}N_2O_4Br=426$

EXAMPLE 18

Preparation of 7-ethyl-5,10-dihydroxycamptothecin

7-Ethyl-10-hydroxycamptothecin (50 mg, 0.128 m-mol) is dissolved in dimethylformamide (20 ml). To this solution are added anhydrous potassium carbonate (150 mg) and iodine (40 mg, 0.157 m-mol), and the mixture is stirred for 5 hours at room temperature. Any insoluble matter is then removed by filtration and the filtrate is evaporated until dryness. The residue is purified by way of column chromatography on silica gel whereby 35 mg (67.0%) of the objective compound is obtained.

¹H-NMR (in DMSO-d₆)δ ppm: 0.90 (3H, t, J=7.5 Hz), 1.30 (3H, t, J=7.5 Hz), 1.90 (2H, q, J=7.5 Hz), 3.30 (2H, q, 7.5 Hz), 5.40 (2H, s), 6.50 (1H, s), 7.0–8.0 (6H, m), 10.30 (1H, s)

MS: m/e 408 [M+], for $C_{22}H_{20}N_2O_6=408$

EXAMPLE 19

Preparation of 7-ethyl-10-hydroxy-5-methoxycamptothecin

7-Ethyl-5,10-dihydroxycamptothecin (20 mg, 0.049 m-mol) is suspended in methanol (30 ml). To this suspension is added conc. sulfuric acid (0.5 ml), and the mixture is stirred for 48 hours. The solvent is then distilled off under reduced pressure and the residue is dissolved in chloroform and washed with water. The chloroform phase is dried with anhydrous magnesium sulfate and then evaporated until dryness under reduced pressure. The residue is purified by way of column chromatography on silica gel whereby the objective compound (18 mg, 87.0%) is obtained.

¹H-NMR (in CDCl₃) ppm: 1.00 (3H, t, J=7.5 Hz), 1.25 (3H, t, J=7.5 Hz), 1.95 (2H, q, J=7.5 Hz), 3.40 (2H, q, J=7.5 Hz), 4.00 (3H, s), 5.44 (2H, ABq,), 6.80–8.10 (5H, m)

MS: m/e 422 [M+], for $C_{23}H_{22}N_2O_6=422$

What is claimed is:

1. A camptothecin derivative of the formula:

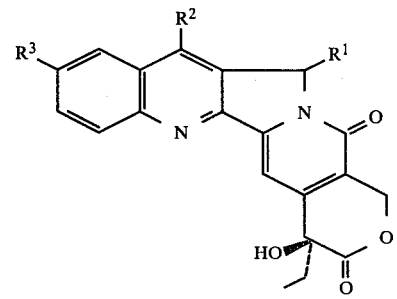

wherein R¹ is a hydrogen atom, a straight or branched C₁–C₃₀ alkyl group, a C₅–C₈ cycloalkyl group, a hydroxyl group, a C₁–C₃₀ alkoxy group or a C₁–C₁₇ acyloxy group, R² is a hydrogen atom, a straight or branched C₁–C₃₀ alkyl group, a C₅–C₈ cycloalkyl group, a phenylalkyl group, a naphthylalkyl group, a hydroxymethyl group, a carboxymethyl group or a C₁–C₁₇ acyloxymethyl group, and R³ is XR' where R' is a hydrogen atom, a straight or branched C₁–C₃₀ alkyl group or a C₁–C₁₇ acyl group and X is an oxygen atom or a sulfur atom or wherein R' is a nitro group, an amino group, a C₁–C₈ alkylamino group, a C₁–C₁₇ acylamino group or a halogen atom, with the proviso that when both $R^1$ and $R^2$ are hydrogen atoms, $R^3$ is not hydroxy, methoxy or acetoxy.

2. A camptothecin derivative of the formula:

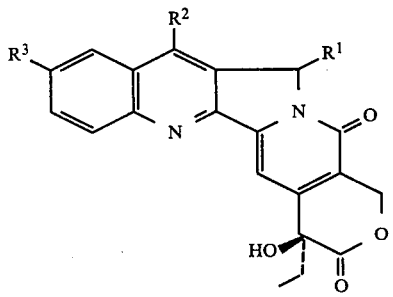

wherein $R^1$ is a hydrogen atom, a straight or branched $C_1$-$C_{18}$ alkyl group, a $C_5$-$C_8$ cycloalkyl group, a hydroxyl group, a $C_1$-$C_{18}$ alkoxy group or a $C_1$-$C_{17}$ acyloxy group, $R^2$ is a hydrogen atom, a straight or branched $C_1$-$C_{18}$ alkyl group, a $C_5$-$C_8$ cycloalkyl group, a phenylalkyl group, a naphthylalkyl group, a hydroxymethyl group, a carboxymethyl group or a $C_1$-$C_{17}$ acyloxymethyl group, and $R^3$ is $XR'$ where $R'$ is a hydrogen atom, a straight or branched $C_1$-$C_{18}$ alkyl group or a $C_1$-$C_{17}$ acyl group and X is an oxygen atom or a sulfur atom or wherein $R'$ is a nitro group, an amino group, a $C_1$-$C_8$ alkylamino group, a $C_1$-$C_{17}$ acylamino group or a halogen atom, with the proviso that when both $R^1$ and $R^2$ are hydrogen atoms, $R^3$ is not hydroxy, methoxy or acetoxy.

3. A camptothecin derivative according to claim 2, wherein $R^3$ is $C_2$-$C_{18}$ alkoxy.

4. A camptothecin derivative according to claim 2, wherein $R^3$ is $C_1$-$C_{18}$ alkylmercapto.

5. A camptothecin derivative according to claim 2, wherein $R^3$ is $C_3$-$C_{18}$ alkanoyloxy.

6. A camptothecin derivative according to claim 2, wherein $R^3$ is phenyl or nicotinyl.

7. A camptothecin derivative according to claim 2, wherein $R^3$ is arylsulfonyloxy.

8. A camptothecin derivative according to claim 2, wherein $R^3$ is hydroxy and $R^1$ is alkyl, alkoxy, or acyloxy.

9. A camptothecin derivative according to claim 2, wherein $R^1$ and $R^3$ are hydroxy.

10. A camptothecin derivative according to claim 2, wherein $R^3$ is hydroxy and $R^2$ is alkyl.

11. A camptothecin derivative according to claim 2, wherein $R^3$ is hydroxy and $R^2$ is phenylalkyl or naphthylalkyl.

12. A camptothecin derivative according to claim 2, wherein $R^3$ is hydroxy and $R^2$ is hydroxymethyl.

13. A camptothecin derivative according to claim 2, wherein $R^3$ is hydroxy and $R^2$ is acyloxymethyl.

14. A camptothecin derivative according to claim 2, wherein $R^2$ and $R^3$ are hydroxy.

15. A camptothecin derivative according to claim 2, wherein $R^3$ is alkoxy and $R^1$ is hydroxy.

16. A camptothecin derivative according to claim 2, wherein $R^3$ is alkyl.

17. A camptothecin derivative according to claim 2, wherein $R^3$ is alkoxy and $R^1$ is alkyl.

18. A camptothecin derivative according to claim 2, wherein $R^1$ and $R^3$ are alkoxy.

19. A camptothecin derivative according to claim 2, wherein $R^3$ is alkoxy and $R^2$ is alkyl.

20. A camptothecin derivative according to claim 2, wherein $R^3$ is alkoxy and $R^2$ is phenylalkyl or naphthylalkyl.

21. A camptothecin derivative according to claim 2, wherein $R^3$ is alkoxy and $R^2$ is hydroxymethyl.

22. A camptothecin derivative according to claim 2, wherein $R^3$ is alkoxy and $R^2$ is acyloxymethyl.

23. A camptothecin derivative according to claim 2, wherein $R^3$ is acyloxy and $R^1$ is alkyl.

24. A camptothecin derivative according to claim 2, wherein $R^3$ is acyloxy and $R^1$ is hydroxy.

25. A camptothecin derivative according to claim 2, wherein $R^1$ and $R^3$ are diacyloxy.

26. A camptothecin derivative according to claim 2, wherein $R^3$ is acyloxy and $R^2$ is alkyl.

27. A camptothecin derivative according to claim 2, wherein $R^3$ is acyloxy and $R^2$ is phenylalkyl or naphthylalkyl.

28. A camptothecin derivative according to claim 2, wherein $R^3$ is acyloxy and $R^2$ is hydroxymethyl.

29. A camptothecin derivative according to claim 2, wherein $R^3$ is acyloxy and $R^2$ is acyloxymethyl.

30. A camptothecin derivative according to claim 2, wherein $R^3$ is nitro.

31. A camptothecin derivative according to claim 2, wherein $R^3$ is amino.

32. A camptothecin derivative according to claim 2, wherein $R^3$ is alkylamino.

33. A camptothecin derivative according to claim 2, wherein $R^3$ is acylamino.

34. A camptothecin derivative according to claim 2, wherein $R^3$ is halogen.

35. A camptothecin derivative according to claim 34, wherein said halogen is chlorine or bromine.

36. The compound 7-ethyl-10-hydroxycamptothecin.

37. A process for the preparation of a 10-substituted camptothecin of the formula:

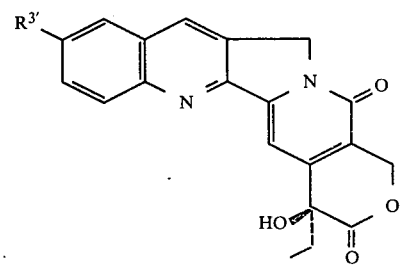

wherein $R^{3'}$ is a nitro group, an amino group, a $C_1$-$C_8$ alkylamino group, a $C_1$-$C_{17}$ acylamino group, a hydroxyl group or a halogen atom which comprises catalytically hydrogenating camptothecin in a solvent under atmospheric pressure in the presence of a noble metal catalyst, treating the resultant 1,2,6,7-tetrahydrocamptothecin with an acylating agent to introduce the acyl group into the 1-position, treating the thus obtained 1-acyl-1,2,6,7-tetrahydrocamptothecin with a mixture of nitric acid and sulfuric acid, eliminating the 1-acyl group in the resultant 1-acyl-10-nitro-1,2,6,7-tetrahydrocamptothecin by hydrolysis under an acidic or alkaline condition, and then treating the resultant 10-nitro-1,2,6,7-tetrahydrocamptothecin with an oxidizing agent for dehydrogenation of the saturated ring, and if desired, reducing the resultant 10-nitrocamptothecin or 10-nitro-1,2,6,7-tetrahydrocamptothecin prior to the dehydrogenation to convert the nitro group into an amino group, and then modifying the amino group by N-alkylation or N-acylation or by diazotization followed by hydrolysis or reaction with a cuprous halide to convert the amino group into a hydroxyl group or a halogen atom, and, if necessary, treating the resulting 10-modified 1,2,6,7-tetrahydrocamptothecin derivative with an oxidizing agent for dehydrogenation of the saturated ring.

38. A process according to claim 37, wherein the noble metal catalyst is platinum black, platinum oxide, palladium black or palladium oxide.

39. A process according to claim 37, wherein the oxidizing agent is DDQ, air or nitric acid.

40. A process according to claim 37, wherein 10-nitro-1,2,6,7-tetrahydrocamptothecin is reduced prior to the oxidation for dehydrogenation of the saturated ring.

41. The process according to claim 38, wherein the noble metal catalyst is carried on carbon black.

* * * * *